US011857525B2

United States Patent
Hamilton-Reeves et al.

(10) Patent No.: US 11,857,525 B2
(45) Date of Patent: Jan. 2, 2024

(54) TREATMENT OR PREVENTION OF SURGERY-INDUCED CACHEXIA AND/OR EXPRESSION OF MYELOID-DERIVED SUPPRESSOR CELLS AND PRO-INFLAMMATORY CYTOKINES

(71) Applicant: SOCIÉTÉ DES PRODUITS NESTLÉ S.A., Vevey (CH)

(72) Inventors: Jill Hamilton-Reeves, Shawnee, KS (US); Jeffrey M. Holzbeierlein, Mission Hills, KS (US); Thomas Yankee, Overland Park, KS (US)

(73) Assignee: Societe des Produits Nestle S.A., Vevey (CH)

( * ) Notice: Subject to any disclaimer, the term of this patent is extended or adjusted under 35 U.S.C. 154(b) by 112 days.

(21) Appl. No.: 15/548,186

(22) PCT Filed: Feb. 15, 2016

(86) PCT No.: PCT/EP2016/053156
§ 371 (c)(1),
(2) Date: Aug. 2, 2017

(87) PCT Pub. No.: WO2016/128576
PCT Pub. Date: Aug. 18, 2016

(65) Prior Publication Data
US 2018/0021279 A1    Jan. 25, 2018

Related U.S. Application Data

(60) Provisional application No. 62/116,155, filed on Feb. 13, 2015.

(51) Int. Cl.
| | | |
|---|---|---|
| A61K 31/198 | (2006.01) | |
| A61K 31/07 | (2006.01) | |
| A61K 31/202 | (2006.01) | |
| A61K 31/70 | (2006.01) | |
| A23L 33/12 | (2016.01) | |
| A23L 33/13 | (2016.01) | |
| A23L 33/14 | (2016.01) | |
| A23L 33/00 | (2016.01) | |
| A23L 33/175 | (2016.01) | |
| A23L 33/155 | (2016.01) | |
| A61K 9/00 | (2006.01) | |
| A61K 31/7088 | (2006.01) | |

(52) U.S. Cl.
CPC .......... *A61K 31/198* (2013.01); *A23L 33/12* (2016.08); *A23L 33/13* (2016.08); *A23L 33/14* (2016.08); *A23L 33/155* (2016.08); *A23L 33/175* (2016.08); *A23L 33/30* (2016.08); *A61K 9/0053* (2013.01); *A61K 9/0095* (2013.01); *A61K 31/07* (2013.01); *A61K 31/202* (2013.01); *A61K 31/70* (2013.01); *A61K 31/7088* (2013.01); *A23V 2002/00* (2013.01)

(58) Field of Classification Search
CPC .......... A23L 33/12; A23L 33/13; A23L 33/14; A23L 33/155; A23L 33/175; A23L 33/30; A23V 2002/00; A61K 31/07; A61K 31/198; A61K 31/202; A61K 31/70; A61K 31/7088; A61K 9/0053; A61K 9/0095; G03C 1/72
USPC ..................................................... 514/44 R
See application file for complete search history.

(56) References Cited

U.S. PATENT DOCUMENTS

2005/0136129 A1* 6/2005 Verheul-Koot ......... A61P 17/02
                                                      514/474
2011/0229521 A1* 9/2011 Schiffrin ................ A61K 33/00
                                                      424/234.1

FOREIGN PATENT DOCUMENTS

| CN | 1810238 | 8/2006 |
| EP | 0378824 | 7/1990 |
| JP | 2014510530 A | 5/2014 |
| WO | 2012130627 | 10/2012 |

OTHER PUBLICATIONS

Vidal-Casariego et al. CLinical Nutrition, 2014, vol. 33, pp. 951-957. (Year: 2014).*
Kesavalu et al. Oral Microbiology and Immunology, vol. 22, No. 4, pp. 232-239. (Year: 2007).*
Gregg et al. J Urol. Jan. 2011 ; 185(1): 90-96. (IDS) (Year: 2011).*
Mathur et al. The British Hournal of Urology, vol. 101, Issue No. 8, 2008, pp. 973-977. (Year: 2008).*

(Continued)

*Primary Examiner* — Janet L Epps-Smith
(74) *Attorney, Agent, or Firm* — K&L Gates LLP

(57) ABSTRACT

A specialized immunonutrition supplement can be administered to a surgical patient to reduce post-operative complications by restraining the expansion of myeloid-derived suppressor cells. The supplement includes one or more of L-arginine, omega-3 fatty acids, vitamin A, and dietary nucleotides, preferably all four of these compounds. The supplement is administered to the patient at least once per day for a time period extending from a pre-operative day that is three to seven days prior to a bladder surgery of the patient to a post-operative day that is three to seven days after the bladder surgery. The supplement can be administered to treat or prevent post-operative paralytic ileus in a bladder cancer patient; treat or prevent surgery-induced, inflammation-induced or cancer-induced cachexia; reduce the incidence of chronic infections resulting from expansion of myeloid-derived suppressor cells in a patient; and/or reduce mRNA expression of pro-inflammatory cytokines in a patient.

9 Claims, 10 Drawing Sheets

(56) References Cited

OTHER PUBLICATIONS

Li et al. "The effect of oxidized low-density lipoprotein combined with adriamycin on the proliferation of Eca-109 cell line" Lipids in Health and Disease, 2011, vol. 10, No. 108, 11 pages.

Kesavalu et al. "Omega-3 fatty acid regulates inflammatory cytokine/mediator messenger RNA expression in Porphyromonas gingivalis-induced experimental periodontal disease" Oral Microbiology and Immunology, 2007, vol. 22, pp. 232-239.

Vidal-Casariego et al. "Efficacy of arginine-enriched enteral formulas in the reduction of surgical complications in head and neck cancer: A systematic review and meta-analysis" Clinical Nutrition, 2014, vol. 33, pp. 951-957.

Orellana, "Nitric Oxide Synthase Inhibitor and Interleukin 18 Improve Antitumour Immunotherapy", Lancet Oncology, vol. 3, Issue No. 1, Jan. 1, 2002, 2 pages.

Ohsawa et al., "Recent Molecular Understanding in Pathophysiology of Cachexia and its Application for Pharmacotherapy", Japanese journal of pharmaceutical palliative care and sciences, vol. 5, 2012, pp. 31-37.

Gianotti et al., "A Randomized Controlled Trial of Preoperative Oral Supplementation With a Specialized Diet in Patients With Gastrointestinal Cancer", Gastroenterology, vol. 122, Issue No. 7, 2002, pp. 1763-1770.

Oral Impact®, Nestle, Nov. 2014, 3 pages.

Drover et al., "Perioperative Use of Arginine-supplemented Diets: A Systematic Review of the Evidence", American college of Surgeons, vol. 212, Issue No. 3, 2010, pp. 385 to 399, 399e1.

Japan Office Action Received for Application No. P2017-538707, dated Oct. 24, 2019, 14 pages(7 pages of English translation and 7 pages of official copy).

Gregg et al., "Effect of Pre-Operative Nutritional Deficiency on Mortality After Radical Cystectomy for Bladder Cancer", The Journal of Urology, vol. 185, Issue No. 1, 2011, pp. 1-14.

Mathur et al., "Changes in Body Composition, Muscle Function and Energy Expenditure After Radical Cystectomy", The British Journal of Urology, vol. 101, Issue No. 8, 2008, pp. 973-977.

Japan Patent Office Communication for Application No. P2020-183624, Dispatch No. 810235, dated Nov. 24, 2021, 7 pages.

* cited by examiner

FIG. 2

Interim Analysis Baseline Characteristics

| | Specialized Immunonutrition Intervention (N=9) | Oral Nutrition Supplement Control (N=7) |
|---|---|---|
| Mean age, y | 65.8 ± 6.1 | 65.0 ± 7.2 |
| Current smoker, No. (%) | | |
| Yes | 4 (44.4%) | 1 (14.3%) |
| No | 5 (55.6%) | 6 (85.7%) |
| Charlson Comorbidity Index | 4.6 ± 0.9 | 4.6 ± 1.3 |
| Clinical Stage, No. (%) | | |
| CIS | 7 (77.8%) | 4 (57.1%) |
| T1 | 1 (11.1%) | 0 (0%) |
| T2a | 0 (0%) | 1 (14.3%) |
| T2b | 1 (11.1%) | 0 (0%) |
| Neoadjuvant Chemotherapy, No. (%) | 5 (55.6%) | 1 (14.3%) |
| Body Mass Index, kg/m² | 24.8 ± 3.1 | 27.3 ± 4.7 |
| PG-SGA Score* | 5.6 ± 4.9 | 8.3 ± 9.5 |

*Patient Generated Subjective Global Assessment

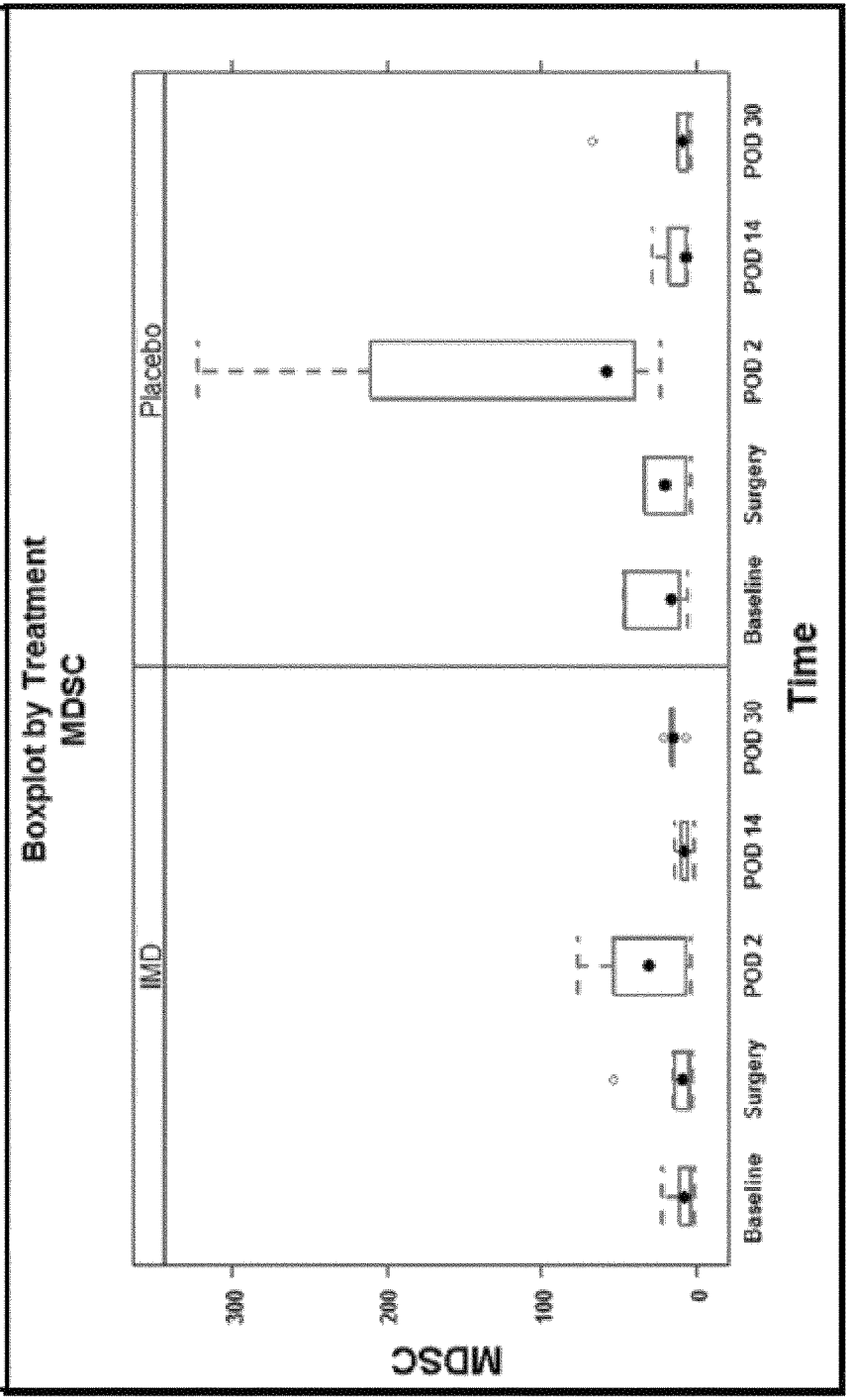

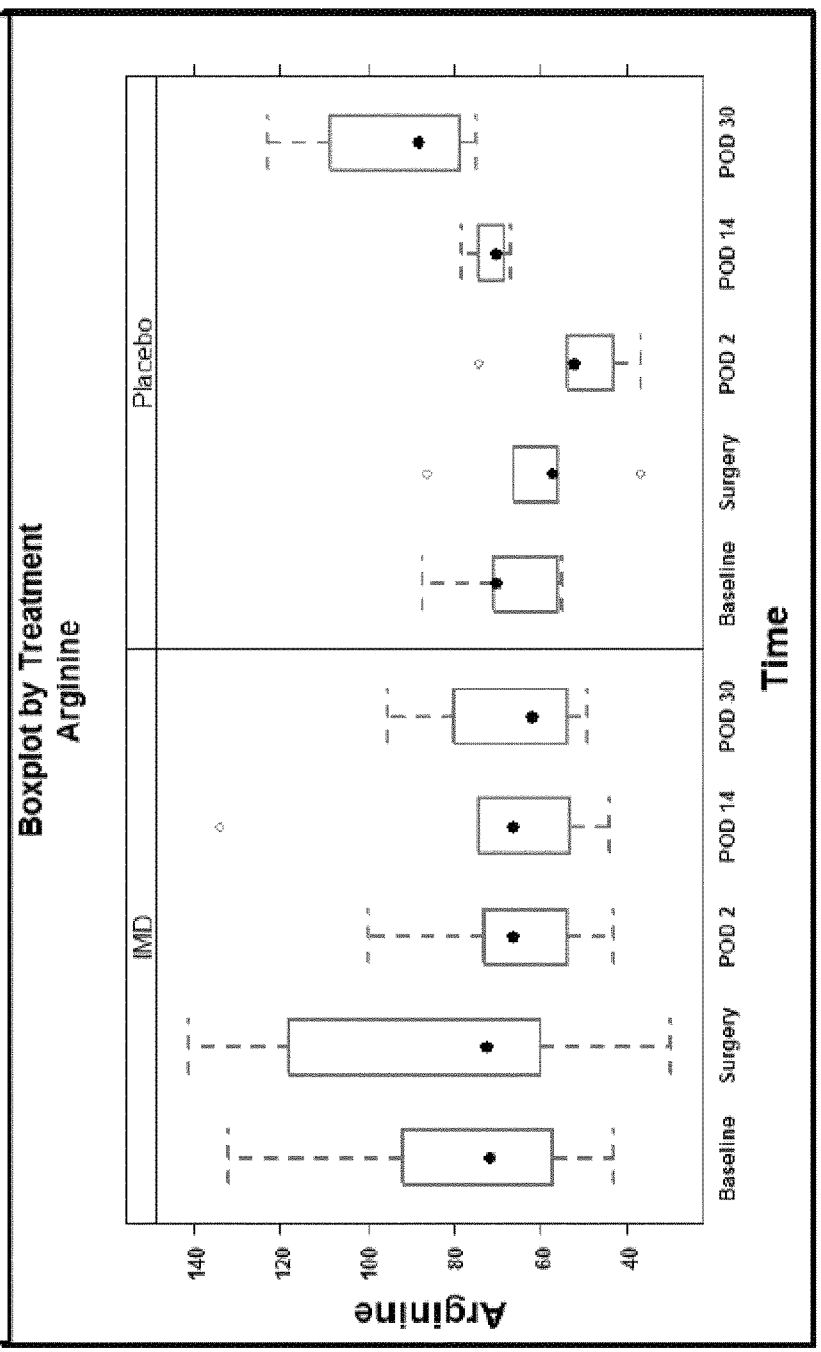
Figure 4- Plasma arginine compared between the IMD and placebo groups over time (preliminary data). IMD = Immune modulating drink (n=9); placebo (n=7)

FIG. 5

Interim Analysis Surgical Complications

| | Specialized Immunonutrition (N=9) | ONS Control (N=6) | P-Value |
|---|---|---|---|
| Antibiotic Use ‡ (%) | | | |
| 30 day | 44 | 50 | 0.82 |
| 90 day | 22 | 67 | 0.08 |
| Intra-Abdominal Infection (%) | | | |
| 30 day | 11 | 33 | 0.29 |
| 90 day | 0 | 0 | NA |
| Surgical Site Infection (%) | | | |
| 30 day | 11 | 17 | 0.74 |
| 90 day | 0 | 17 | 0.20 |

† Clavien-Dindo Grade IIIa and above
‡ Excludes prophylaxis

Figure 7. Relative Skeletal Muscle Index compared between the IMD and placebo groups over time (preliminary data). IMD = Immune modulating drink (n=9, baseline; n=7 POD 14 & 30); placebo (n=7, baseline; n=3, POD 14; n=5, POD 30)

FIG. 9
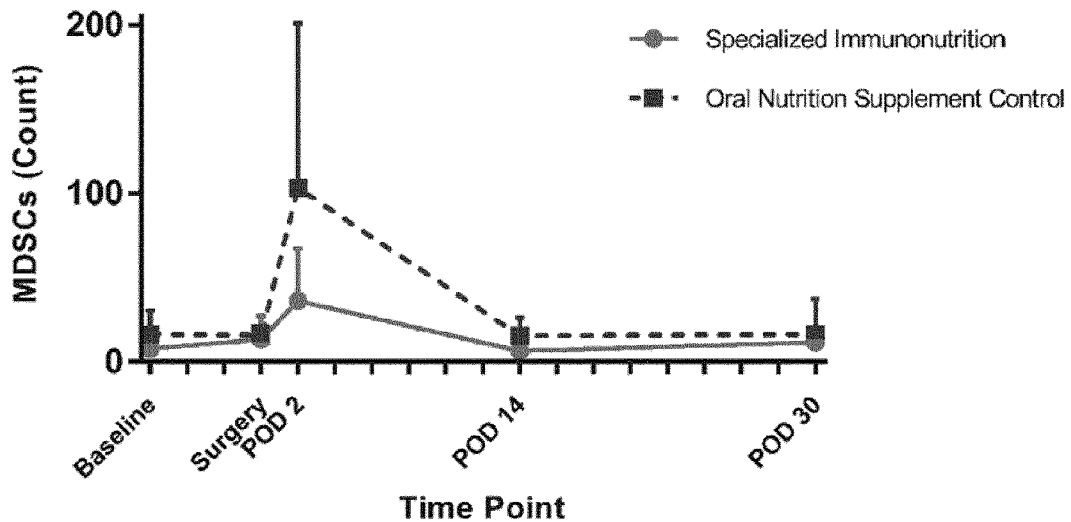
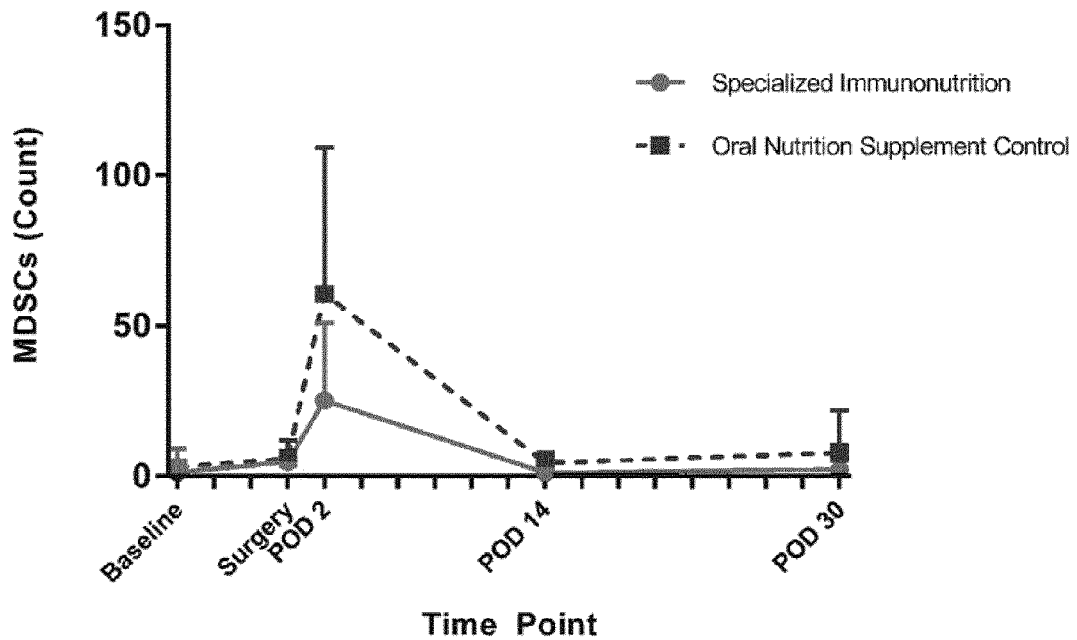

Postoperative complications of men after bladder cancer surgery[1]

| | Specialized immunonutrition, n = 14 men | Oral nutrition supplement, n = 15 men | Differences between groups, % (95% CI) |
|---|---|---|---|
| Complications, n (%) | | | |
| 30 d | 10 (71) | 11 (73) | -2 (-36 to 33) |
| 90 d* | 2 (14) | 7 (47) | -33 (-70 to -5.7) |
| High-grade complications, n(%) | | | |
| 30 d | 2 (14) | 2 (13) | 1 (-25 to 27) |
| 90 d | 0 (0) | 2 (13) | -13 (-37 to 11) |
| Antibiotic use, n (%)[2] | | | |
| 30 d | 5 (36) | 9 (60) | -24 (-66 to 18) |
| 90 d** | 2 (14) | 8 (53) | -39 (-77 to -0.94) |
| Intra-abdominal infection, n (%) | | | |
| 30 d | 1 (7) | 4 (27) | -20 (-53 to 14) |
| 90 d | 0 (0) | 1 (7) | -7 (-26 to 13) |
| Ileus > 5 d, n (%) | 4 (27) | 2 (13) | 14 (-21 to 51) |
| Length of stay | 6.3 (3.1) | 6.1 (1.9) | 0.2 (-1.79 to 2.23) |
| SIRS, n (%)[3] | 1 (7) | 2 (13) | -6 (-34 to 22) |
| Readmission, n (%) | | | |
| Yes | 4 (29) | 6 (40) | -11 (-53 to 30) |
| No | 10 (71) | 9 (60) | 11 (-29 to 53) |
| Clavien-Dindo grade 30 d, n (%)[4] | | | |
| Grade 0 | 0 (0) | 0 (0) | |
| Grade 1 | 2 (14) | 1 (7) | 7 (-22 to 37) |
| Grade 2 | 8 (57) | 8 (53) | 4 (-36 to 44) |
| Grade 3a | 0 (0) | 1 (7) | -7 (-26 to 13) |
| Grade 3b | 0 (0) | 1 (7) | -7 (-26 to 13) |
| Grade 4-5 | 0 (0) | 0 (0) | |
| Clavien-Dindo grade 90 d, n (%) | | | |
| Grade 0 | 0 (0) | 0 (0) | |
| Grade 1 | 0 (0) | 0 (0) | |
| Grade 2 | 2 (14) | 5 (33) | -19 (-56 to 18) |
| Grade 3a | 0 (0) | 2 (13) | -13 (-37 to 11) |
| Grade 3b | 0 (0) | 0 (0) | |
| Grade 4-5 | 0 (0) | 0 (0) | |

FIG. 10

TREATMENT OR PREVENTION OF SURGERY-INDUCED CACHEXIA AND/OR EXPRESSION OF MYELOID-DERIVED SUPPRESSOR CELLS AND PRO-INFLAMMATORY CYTOKINES

CROSS REFERENCE TO RELATED APPLICATIONS

The present application is a National Stage of International Application No. PCT/EP2016/053156, filed on Feb. 15, 2016, which claims priority to U.S. Provisional Patent Application No. 62/116,155, filed on Feb. 13, 2015, the entire contents of which are being incorporated herein by reference.

BACKGROUND

The present disclosure generally relates to compositions and methods that treat or prevent surgery-induced cachexia and/or expression of myeloid-derived suppressor cells and pro-inflammatory cytokines. More specifically, the present disclosure relates to compositions comprising one or more of L-arginine, omega-3 fatty acids, vitamin A, and dietary nucleotides and further relates to methods comprising administering such compositions to a patient.

Cachexia is a severe body wasting condition characterized by marked weight loss, anorexia, asthenia, and anaemia. Cachexia is a common feature of a number of illnesses, such as cancer, sepsis, chronic heart failure, rheumatoid arthritis, and acquired immune deficiency syndrome (AIDS). Moreover, patients undergoing surgery typically lose significant amounts of muscle mass.

Certain tumors may induce cachexia. Cancer cachexia is irreversible and once it is refractory, contributes to death. Cancer cachexia is characterized by rapid muscle wasting, systemic inflammation, and anorexia that cannot be reversed by increased food intake. Although Radical Cystoprostatectomy (RC) with urinary diversion is the gold standard for treatment of invasive bladder cancer in men (i.e., surgically removing the bladder and reconstructing the urinary tract with portions of the terminal ileum), surgical stress leads to a catabolic state and an impaired immune response resulting in pre-cachexia and cachexia. On average, RC surgery leads to a 5% loss in body weight and 7% loss in muscle mass by two weeks post-surgery, with full recovery of skeletal muscle not achieved by even six months past the surgery. RC surgery lasts about 6 hours, and the prevalence of ileus (paralyzed gut) is very high because the surgery involves extensive bowel manipulation and a long duration of anesthesia. Moreover, RC surgery has a 70% incidence rate of systemic inflammatory response syndrome (SIRS) and a 25% post-operative infection rate, suggesting that some bladder cancer patients undergoing RC surgery experience an exaggerated adaptive immune suppression and inflammation response.

SUMMARY

The present inventors found that over the last 2 years, 65% of RC patients developed pre-cachexia or cachexia and 25% of these patients died. Surgery induces myeloid-derived suppressor cells (MDSC) that express arginase 1 (ARG1) and deplete arginine concentrations leading to T cell dysfunction. Data from the RC patients showed an influx of MDSCs three hours post-incision that peaked two days post-operatively and in some patients remained elevated for two weeks. Prolonged elevation of MDSCs increases production of suppressive cytokines and reactive oxygen species and depletes arginine through an increased expression of arginase 1. The skeletal muscle wasting, elevated pro-inflammatory cytokines, and SIRS observed in RC patients implicates surgery via MDSCs as an initiating event of pre-cachexia in some RC patients. Therefore, the long-term goal of the present inventors was to target the initiating mechanisms and prevent the progression of RC-induced cachexia.

Under conditions of physical injury, improving arginine homeostasis restores T lymphocyte counts. Furthermore, adding omega-3 fatty acids and nucleotides to a diet with ample arginine levels prevents the up-regulation of ARG1 expressing MDSCs. A combination of the immune-modulating factors, consisting of arginine, omega-3 fatty acids, and nucleotides on a foundation of a balanced oral or enteral composition that provides a balance of protein, lipids, carbohydrates, minerals and micronutrients, prevents arginine deficiency and blunts the up-regulation of MDSCs. Data from the experimental examples disclosed herein suggests that administering an immune modulating drink (IMD) containing these ingredients before and after surgery reduces surgical complications, including infections and breakdown of wounds, and leads to shorter hospital stays. Patients with cancer of the colorectum, stomach, or pancreas consuming an IMD before and after surgery showed reduced post-operative infections regardless of their nutrition status beforehand. While the mechanisms are still being elucidated, the present inventors believe, without being bound by theory, that adequate arginine improves host immune response and controls the inflammatory responses. The data disclosed herein suggests that preventing arginine deficiency and blunting the up-regulation of ARG1 expressing MDSCs leads to a more balanced immune state and reduced RC-induced cachexia and post-operative complications.

Specifically, the experimental example detailed herein demonstrated the feasibility of peri-operative oral supplementation in men with bladder cancer undergoing a radical cystoprostatectomy. The data from this single-blinded placebo-controlled pilot study shows anti-inflammatory effects, reduced weight loss, and fewer post-operative complications in the treatment group (arginine, fish oil, and nucleotides) compared to the control group. The importance of these findings is that 65% of these patients typically develop cachexia (rapid muscle wasting) after this surgery and 50-64% of these patients experience significant post-operative complications. The study evaluated the immunology and initiating mechanisms of cachexia and discovered important signals therein.

In this regard, the study demonstrated the feasibility of peri-operative feeding by mouth in bladder cancer surgery patients. Furthermore, the study demonstrated that specialized immunonutrition may blunt the expansion of MDSCs and may help stabilize plasma arginine compared to standard oral nutritional supplements (ONS); may reduce 90-day infections compared to ONS; may show less profound weight loss as compared to ONS. Moreover, specialized immunonutrition intake before and after surgery may lead to a reduction in the mRNA expression of pro-inflammatory cytokines. Specialized immunonutrition may reduce the inflammatory environment after surgery and may protect against muscle wasting.

Accordingly, in a general embodiment, the present disclosure provides a method of preventing or reducing the expression of myeloid-derived suppressor cells and pro-inflammatory cytokines post-surgery and/or preventing or reducing the incidence of chronic infections brought on by expansion of myeloid-derived suppressor cells by restraining the expression of myeloid-derived suppressor cells. The method comprises administering to a surgical patient a specialized immunonutrition supplement comprising a component selected from the group consisting of L-arginine, omega-3 fatty acids, vitamin A, nucleotides, and mixtures thereof The supplement is administered to the patient at least once per day for a time period extending from a pre-operative day that is three to seven days prior to a bladder surgery of the patient to a post-operative day that is three to seven days after the bladder surgery.

In an embodiment, the supplement comprises L-arginine and is administered to the surgical patient in a daily dose that provides between about 5 g and about 30 g of the L-arginine per day.

In an embodiment, the supplement comprises omega-3 fatty acids and is administered to the surgical patient in a daily dose that provides an amount of the omega-3 fatty acids that comprises about 0.5 g to about 10.0 g of eicosapentaenoic acid and docosahexaenoic acid in total per day.

In an embodiment, the supplement comprises Vitamin A and is administered to the surgical patient in a daily dose that provides at least about 500 μg RE of the Vitamin A per day.

In an embodiment, the supplement comprises nucleotides and is administered to the surgical patient in a daily dose that provides between about 0.5 and about 10.0 mg of nucleotides per day.

In an embodiment, the component comprises L-arginine, omega-3 fatty acids, and nucleotides. The component can further comprise Vitamin A.

In an embodiment, the supplement comprises nucleotides, and at least a portion of the nucleotides are provided by polymeric yeast RNA and/or derived from yeast RNA.

In an embodiment, the supplement is orally administered to the surgical patient. In an embodiment, the supplement is a drink.

In an embodiment, the supplement is in a form selected from a tablet, a capsule, a powder or a liquid.

In an embodiment, the supplement further comprises an additional component selected from the group consisting of a protein, a carbohydrate, a lipid, and mixtures thereof In an embodiment, the surgical patient has bladder cancer associated with a tumor, and the bladder surgery comprises removal of all or part of the tumor. The surgical patient can be undergoing neoadjuvant therapy before the bladder surgery, and the neoadjuvant therapy can comprise chemotherapy and/or immunotherapy.

In another embodiment, the present disclosure provides a method of treating or preventing cachexia induced by at least one of surgery, cancer or infection in a patient. The method comprises administering to the patient a specialized immunonutrition supplement comprising a component selected from the group consisting of L-arginine, omega-3 fatty acids, vitamin A, nucleotides, and mixtures thereof.

In an embodiment, the cachexia is induced by surgery, and the supplement is administered to the patient at least once per day for a time period extending from a pre-operative day that is three to seven days prior to the surgery of the patient to a post-operative day that is three to seven days after the surgery. The surgery can be associated with muscle and fat catabolism in the patient, an immunosuppressive environment in the patient, and/or an inflammatory environment in the patient.

In an embodiment, the cachexia is induced by cancer associated with a tumor and treated by a surgery comprising removal of all or part of the tumor. The supplement can be administered to the patient at least once per day for a time period extending from a pre-operative day that is three to seven days prior to the surgery to a post-operative day that is three to seven days after the surgery.

In an embodiment, the cachexia is induced by infection.

In an embodiment, the supplement comprises L-arginine and is administered to the patient in a daily dose that provides between about 5 g and about 30 g of the L-arginine per day.

In an embodiment, the component comprises L-arginine, omega-3 fatty acids, and nucleotides. The component can further comprise Vitamin A.

In an embodiment, the present disclosure provides a method of reducing the incidence of chronic infections resulting from expansion of myeloid-derived suppressor cells in a patient. The method comprises administering to the patient a specialized immunonutrition supplement comprising a component selected from the group consisting of L-arginine, omega-3 fatty acids, vitamin A, nucleotides, and mixtures thereof.

In an embodiment, the patient has or is at risk of a *Staphylococcus aureus* infection.

In an embodiment, the patient has a tumor, and the supplement is administered to the patient at least once per day for a time period extending from a pre-operative day that is three to seven days prior to removal of all or part of the tumor to a post-operative day that is three to seven days after the removal. The patient can have bladder cancer associated with the tumor.

In an embodiment, the supplement comprises L-arginine and is administered to the patient in a daily dose that provides between about 5 g and about 30 g of the L-arginine per day.

In an embodiment, the component comprises L-arginine, omega-3 fatty acids, and nucleotides. The component can further comprise Vitamin A.

In another embodiment, the present disclosure provides a method of reducing mRNA expression of pro-inflammatory cytokines in a patient. The method comprises administering to the patient a specialized immunonutrition supplement comprising a component selected from the group consisting of L-arginine, omega-3 fatty acids, vitamin A, nucleotides, and mixtures thereof.

In an embodiment, the patient has or is at risk of systemic inflammatory response syndrome.

In an embodiment, the patient has a tumor, and the supplement is administered to the patient at least once per day for a time period extending from a pre-operative day that is three to seven days prior to removal of all or part of the tumor to a post-operative day that is three to seven days after the removal.

In an embodiment, the supplement is administered to the patient at least once per day for a time period extending from a pre-operative day that is three to seven days prior to a surgery that causes an immunosuppressive environment in the patient to a post-operative day that is three to seven days after the surgery.

In an embodiment, the supplement is administered to the patient at least once per day for a time period extending from a pre-operative day that is three to seven days prior to a surgery that causes an inflammatory environment in the patient to a post-operative day that is three to seven days after the removal.

In an embodiment, the supplement comprises L-arginine and is administered to the patient in a daily dose that provides between about 5 g and about 30 g of L-arginine per day.

In an embodiment, the component comprises L-arginine, omega-3 fatty acids, and nucleotides. The component can further comprise Vitamin A.

In another embodiment, the present disclosure provides a method of treating or preventing post-operative paralytic ileus in a bladder cancer patient. The method comprises administering to the patient a specialized immunonutrition supplement comprising a component selected from the group consisting of L-arginine, omega-3 fatty acids, vitamin A, nucleotides, and mixtures thereof, the supplement is administered to the patient at least once per day for a time period extending from a pre-operative day that is three to seven days prior to a bladder surgery of the patient to a post-operative day that is three to seven days after the bladder surgery.

In an embodiment, the surgery comprises radical cystoprostatectomy with urinary diversion.

In an embodiment, the supplement comprises L-arginine and is administered to the patient in a daily dose that provides between about 5 g and about 30 g of L-arginine per day.

In an embodiment, the component comprises L-arginine, omega-3 fatty acids, and nucleotides. The component can further comprise Vitamin A.

In another embodiment, the present disclosure provides a specialized immunonutrition supplement for use in treating a bladder cancer patient to reduce post-operative inflammation by restraining the expression of myeloid-derived suppressor cells. The supplement comprises an effective amount of a component selected from the group consisting of L-arginine, omega-3 fatty acids, vitamin A, nucleotides, and mixtures thereof. The component can comprise L-arginine, omega-3 fatty acids, and nucleotides and can further comprise Vitamin A.

An advantage of one or more embodiments provided by the present disclosure is to use peri-operative consumption of specialized immunonutrition drinks to prevent cachexia, regulate the adaptive immune response via blunting the expansion of myeloid-derived suppressor cells, and/or resolve inflammation after surgery.

Another advantage of one or more embodiments provided by the present disclosure is to use specialized immunonutrition drinks to improve bladder cancer surgery post-operative outcomes (e.g., reduce post-operative infections and paralytic ileus).

Yet another advantage of one or more embodiments provided by the present disclosure is to use specialized immunonutrition drinks to prevent the onset of cachexia after major surgeries associated with muscle and fat catabolism.

Still another advantage of one or more embodiments provided by the present disclosure is to improve outcomes in bladder cancer surgery patients undergoing neoadjuvant chemotherapy.

An additional advantage of one or more embodiments provided by the present disclosure is to reduce the incidence of chronic infections brought on by the expansion of myeloid-derived suppressor cells.

Another advantage of one or more embodiments provided by the present disclosure is to address the skeletal muscle wasting common in patients undergoing bladder removal surgery in cancer treatment, using specialized immunonutrition drinks.

Yet another advantage of one or more embodiments provided by the present disclosure is to fill a critical need in a patient population at high risk for significant surgical morbidity and mortality.

Still another advantage of one or more embodiments provided by the present disclosure is to capture data sufficient to effectively change the standards of clinical practice.

An additional advantage of one or more embodiments provided by the present disclosure is to optimize the post-surgery feeding protocol for patients undergoing bladder removal surgery in cancer treatment.

Another advantage of one or more embodiments provided by the present disclosure is to provide a nutrition protocol that is currently not part of the standard of care for patients undergoing bladder removal surgery in cancer treatment.

Additional features and advantages are described herein, and will be apparent from, the following Detailed Description and the Figures.

BRIEF DESCRIPTION OF THE FIGURES

FIG. 2 is a table showing the baseline characteristics of the participants in the first experimental study disclosed herein.

FIG. 3 is a graph showing the myeloid-derived suppressor cell counts in the inventive group and the control group over time in the first experimental study disclosed herein.

FIG. 4 is a graph showing the plasma arginine in the inventive group and the control group over time in the first experimental study disclosed herein.

FIG. 5 is a table showing the surgical complications in the inventive group and the control group in the first experimental study disclosed herein.

FIGS. 9A and 9B are graphs of mean counts (plus standard deviation) of total myeloid-derived suppressor cells at five time points before and after radical cystectomy in the inventive group and the control group in the second experimental study disclosed herein.

FIG. 10 is a table identifying post-operative complications in mean after bladder cancer surgery in the inventive group and the control group in the second experimental study disclosed herein.

DETAILED DESCRIPTION

Figure 1:
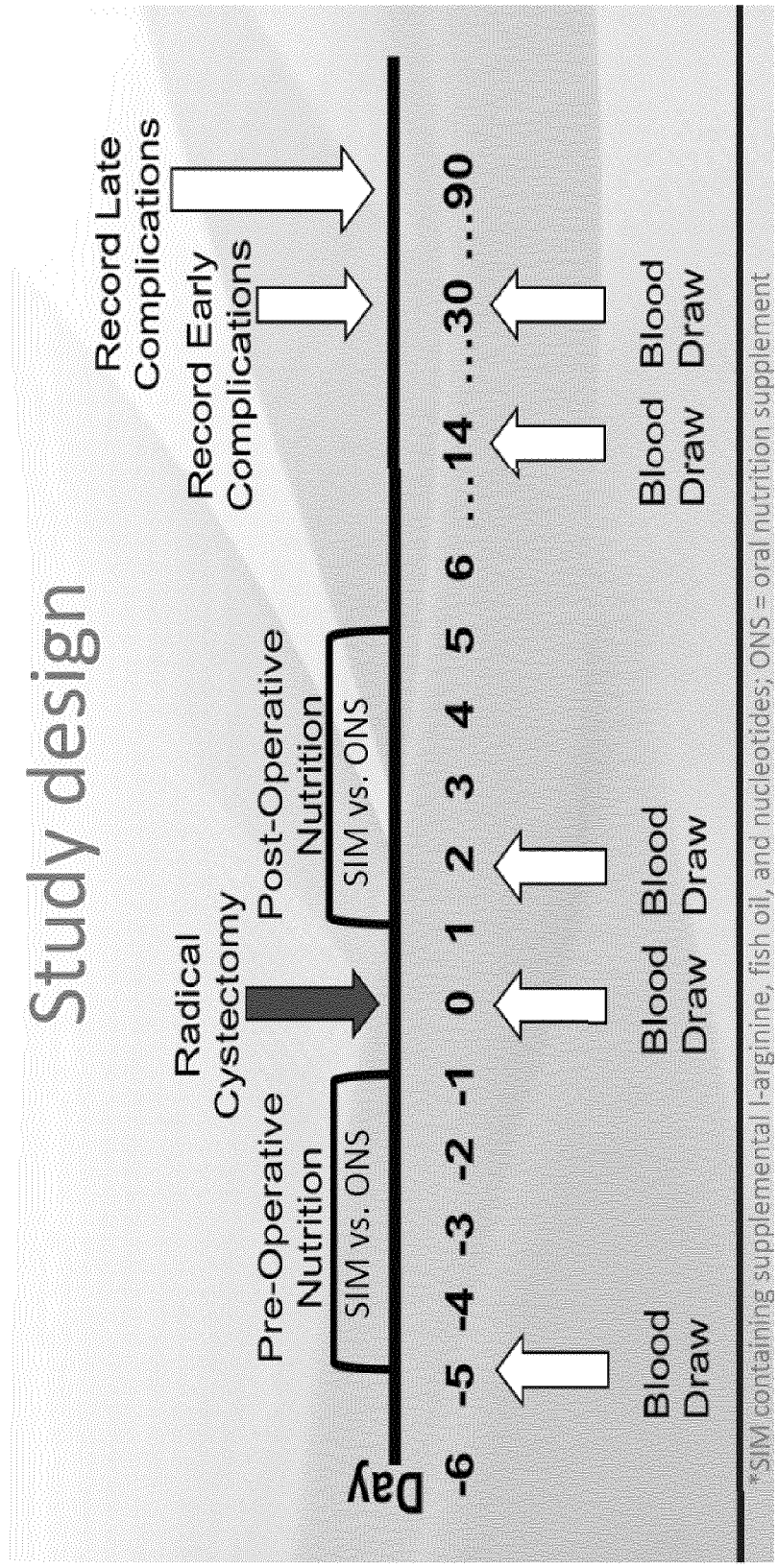
FIG. 1 is a schematic diagram showing the study design used in the first experimental study disclosed herein.

All percentages expressed herein are by weight of the total weight of the composition unless expressed otherwise. As used herein, "about" is understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms "a," "an" and "the" include plural referents unless the context clearly dictates otherwise. Thus, for example, reference to "a component" or "the component" includes two or more components.

The words "comprise," "comprises" and "comprising" are to be interpreted inclusively rather than exclusively. Likewise, the terms "include," "including" and "or" should all be construed to be inclusive, unless such a construction is clearly prohibited from the context. Nevertheless, the compositions disclosed herein may lack any element that is not specifically disclosed herein. Thus, a disclosure of an embodiment using the term "comprising" includes a disclosure of embodiments "consisting essentially of" and "consisting of" the components identified.

The term "and/or" used in the context of "X and/or Y" should be interpreted as "X," or "Y," or "X and Y." Where used herein, the terms "example" and "such as," particularly when followed by a listing of terms, are merely exemplary and illustrative and should not be deemed to be exclusive or comprehensive. As used herein, "associated with" means occurring concurrently, preferably means caused by the same underlying condition, and most preferably means that one of the identified conditions is caused by the other identified condition.

"Prevention" includes reduction of risk and/or severity of a condition or disorder. The terms "treatment," "treat" and "to alleviate" include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms "treatment" and "treat" also refer to the maintenance and/or promotion of health in an individual not suffering from a disease but who may be susceptible to the development of an unhealthy condition. The terms "treatment," "treat" and "to alleviate" are also intended to include the potentiation or otherwise enhancement of one or more primary prophylactic or therapeutic measure. The terms "treatment," "treat" and "to alleviate" are further intended to include the dietary management of a disease or condition or the dietary management for prophylaxis or prevention a disease or condition. A treatment can be patient- or doctor-related.

As used herein, the term "peri-operative period" refers to the time period surrounding a patient's surgical procedure; this commonly includes ward admission, anesthesia, surgery, and recovery. Peri-operative generally refers to the three phases of surgery: preoperative, intraoperative, and post-operative. The goal of peri-operative care is to provide better conditions for patients before operation, during operation, and after operation, including neoadjuvant treatment.

As used herein, the term "neoadjuvant" or "neoadjuvant treatment" refers to a treatment in an effort to make a neoplasm/tumor more amicable to a more aggressive treatment such as bladder removal. Non-limiting examples of neoadjuvant treatments include centralizing the tumor, shrinking the tumor, and reducing the risk of cancer cell seeding during surgical removal, with particular non-limiting examples being chemo- and/or radio-therapies prior to surgical intervention. Traditional cancer therapy includes multiple administrations of chemo-, radio- and/or immuno-therapy; the neoadjuvant strategy is to use fewer doses of chemo- or radio-therapy in an effort to reduce the growth rate or size of the tumor prior to the major intervention (e.g., surgery or more aggressive chemotherapy regimens that remove all or part of the tumor).

"Pre-cachexia" is defined as weight loss >1 kg but <5% of usual body weight/6 months and typically is accompanied by appetite loss.

As used herein, an "effective amount" is an amount that prevents a deficiency, treats a disease or medical condition in an individual or, more generally, reduces symptoms, manages progression of the diseases or provides a nutritional, physiological, or medical benefit to the individual. The relative terms "improved," "increased," "enhanced" and the like refer to the effects of the composition comprising a component selected from the group consisting of L-arginine, omega-3 fatty acids, vitamin A, nucleotides derived from yeast, and combinations thereof (disclosed herein) relative to a composition lacking the component but otherwise identical.

As set forth above, the present inventors found that supplementation with an immune-modulating drink that contains arginine, fish oil, and dietary nucleotides before and after RC surgery led to a reduction in mRNA levels of cytokines associated with helper T cell activity. Pro-inflammatory cytokines and pathways were reduced, suggesting that the immune-modulating drink may reduce the inflammatory environment after surgery, and reduce post-operative complications, especially cachexia.

Accordingly, an aspect of the present disclosure is a method of treating a bladder cancer patient to reduce post-operative complications by restraining the expansion of myeloid-derived suppressor cells. Another aspect of the present disclosure is a method of treating or preventing post-operative paralytic ileus in a bladder cancer patient.

These methods comprise administering to the patient an effective amount of a specialized immunonutrition supplement comprising a component (e.g., an active ingredient) selected from the group consisting of L-arginine, omega-3 fatty acids, vitamin A, nucleotides, and combinations thereof, preferably at least L-arginine. More preferably the supplement comprises L-arginine, omega-3 fatty acids, and nucleotides. Most preferably the supplement further comprises vitamin A in addition to L-arginine, omega-3 fatty acids, and nucleotides; nevertheless, in some embodiments vitamin A is present (e.g., it is the main active ingredient) and one or more of L-arginine, omega-3 fatty acids, and nucleotides. The supplement is administered to the patient at least once per day for a time period extending from a pre-operative day that is three to seven days prior to a bladder surgery of the patient to a post-operative day that is three to seven days after the bladder surgery.

In some embodiments, the time period begins three to seven days prior to the bladder surgery (i.e., there is no administration before three to seven days prior to the bladder surgery); in other embodiments the administration can be begin earlier than three to seven days prior to the bladder surgery. Similarly, in some embodiments, the time period ends three to seven days after the bladder surgery (i.e., there is no administration later than three to seven days after the bladder surgery); in other embodiments the administration can continue beyond three to seven days after the bladder surgery.

In an embodiment, the time period during which the supplement is administered daily extends from at least five days before the bladder surgery to at least five days after the bladder surgery. Preferably the supplement is administered enterally, for example orally, e.g., as a drink. For example, the supplement may be in medical food or beverage product form, e.g. in form of a powder for dissolution. The powder may be combined with a liquid, e.g. water or other liquid such as milk or fruit juice, for example in a ratio of powder to liquid of about 1 to about 5, to obtain a ready-to-consume composition, e.g., ready-to-drink composition or instant drink.

In other aspects, the present disclosure provides a method of treating or preventing surgery-induced cachexia, reducing the incidence of chronic infections resulting from expansion of myeloid-derived suppressor cells in a patient, and a method of reducing mRNA expression of pro-inflammatory cytokines in a patient. Each of these methods comprises administering to the patient a specialized immunonutrition supplement comprising a component (e.g., an active ingredient) selected from the group consisting of L-arginine, omega-3 fatty acids, vitamin A, nucleotides, and mixtures thereof, preferably at least L-arginine. More preferably the supplement comprises L-arginine, omega-3 fatty acids, and nucleotides. Most preferably the supplement further comprises vitamin A in addition to L-arginine, omega-3 fatty acids, and nucleotides; nevertheless, in some embodiments vitamin A is present (e.g., it is the main active ingredient) and one or more of L-arginine, omega-3 fatty acids, and nucleotides.

In some embodiments, the supplement is administered to the patient at least once per day for a time period extending from a pre-operative day that is three to seven days prior to a surgery of the patient to a post-operative day that is three to seven days after the bladder surgery. The surgery can comprise radical cystoprostatectomy with urinary diversion, but the present disclosure is not limited to this specific embodiment of the surgery. For example, the methods disclosed herein extend to other types of cancers and also encompass any surgery in which all or part of a tumor is removed.

In this regard, the expansion of MDSCs leads to immunosuppression and is associated with chronic infections, cancer disease, and cancer progression. The data disclosed herein which shows that specialized immunonutrition prevents the expansion of MDSCs presents opportunities reaching far beyond bladder cancer surgery to the broader oncology surgical population, for example utilization of specialized immunonutrition in cancer therapeutic adjuvant treatments in hematological malignancies and other solid tumors.

Furthermore, blunting MDSC expansion reaches even beyond cancer because an immunosuppressive environment sustains chronic infections. For example, data has shown the negative implications of MDSC expansion on *Staphylococcus aureus* infections (Tebartz et al., 2014). Therefore, specialized immunonutrition may be a relevant adjuvant treatment for the growing problem of Methicillin-resistant *Staphylococcus aureus* (MRSA). Therefore, the composition can be administered to a patient having an infection or at risk of an infection.

In summary, an immunosuppressive environment sustains chronic infection, and specialized immunonutrition blunting MDSC expansion would benefit many patients.

Moreover, the mechanistic data shows effects beyond immune function. For example, the study disclosed herein shows that intake of the specialized immunonutrition supplement before and after surgery led to a reduction in the mRNA expression of pro-inflammatory cytokines. Therefore, the specialized immunonutrition supplement may reduce the inflammatory environment after surgery. RC surgery has a 70% incidence rate of systemic inflammatory response syndrome (SIRS) (Haga et al., 1997), and the risk of mortality increases substantially when SIRS progresses to multiple organ dysfunction syndrome. Recent clinical trials trying to prevent SIRS have been unsuccessful, but the data disclosed herein suggests that the balance between pro- and anti-inflammatory mediators may be more appropriate.

Still further, the treatment or prevention of cachexia by the supplement can extend to non-cancer surgeries, for example surgeries associated with muscle and fat catabolism. As another example, the supplement can treat or prevent cachexia associated with an inflammatory and/or immunosuppressive environment from a surgery.

In each of the methods disclosed herein, the daily dose of the specialized immunonutrition supplement preferably provides between about 5 g to about 30 g of the L-arginine per day, more preferably about 10 g to about 15 g of the L-arginine per day per day. The daily dose of the supplement preferably provides an amount of the omega-3 fatty acids that comprises about 0.5 g to about 10.0 g of eicosapentaenoic acid (EPA, 20:5n-3) and docosahexaenoic acid (DHA, 22:6n-3) in total per day, more preferably about 1.0 g to about 5.0 g of the EPA and the DHA total per day. In an embodiment, the supplement comprises fish oil that provides at least a portion of the omega-3 fatty acids.

The daily dose of the supplement preferably pro-vides between about 0.5 g and about 10.0 g of the nucleotides, more preferably about 1.0 to 5.0 g of the nucleotides. As used herein, a "nucleotide" is understood to be a subunit of deoxyribonucleic acid ("DNA") or ribo-nucleic acid ("RNA"). A nucleotide is an organic compound made up of a nitrogenous base, a phosphate molecule, and a sugar molecule (deoxyribose in DNA, and ribose in RNA). Individual nucleotide monomers (single units) are linked together to form polymers, or long chains. Exogenous nucleotides are specifically provided by dietary supplementation. The exogenous nucleotide can be in a monomeric form such as, for example, 5'-Adenosine Monophosphate ("5'-AMP"), 5'-Guanosine Monophosphate ("5'-GMP"), 5'-Cytosine Monophosphate ("5'-CMP"), 5'-Uracil Monophosphate ("5'-UMP"), 5'-Inosine Monophosphate ("5'-IMP"), 5'-Thymine Monophosphate ("5'-TMP"), or combinations thereof. The exogenous nucleotide can also be in a polymeric form such as, for example, intact RNA. The nucleotides are preferably provided by polymeric yeast RNA and/or derived from yeast RNA.

The daily dose of the specialized immunonutrition supplement preferably provides at least about 500 μg RE of the Vitamin A per day.

The supplement can comprise protein in an amount of about 20% to about 40% of the energy content of the supplement. The protein can be whey, e.g., native whey, intact unhydrolyzed whey, whey protein concentrate, whey protein isolate or whey protein hydrolysate; casein; a vegetable protein such as soy protein; and combinations thereof. The casein may be provided in free form or in the form of a salt, for example, a sodium salt, a calcium salt or a potassium salt. Although the protein can comprise vegetable protein, in some embodiments the supplement is gluten-free.

The protein may be extensively hydrolyzed protein hydrolysates prepared from acid or enzyme treated animal and vegetable proteins, such as casein hydrolysate, whey hydrolysate, casein/whey hydrolysate, soy hydrolysate, and mixtures thereof "Extensively hydrolyzed" protein hydrolysates means that the intact protein is hydrolyzed into peptide fragments in which a majority of the peptide fragments have a molecular weight less than 1,000 Daltons, preferably at least about 75% and most preferably at least about 95% of the peptide fragments having a molecular weight less than about 1,000 Daltons. Free amino acids and synthetic short peptide chains may be substituted for or added to the protein hydrolysates.

Carbohydrates may provide an energy content of about 30% to about 50% of the supplement. In an embodiment, the carbohydrate source is selected from the group consisting of maltodextrin; native or modified starch from tapioca, corn, rice, other cereals, or potato; high amylose starch; a disaccharide such as sucrose; a monosaccharide such as glucose or fructose; and mixtures thereof. In an embodiment, the supplement has a maximum of 0.2 g lactose per 100 kcal, preferably less than 0.17 g lactose per 100 kcal.

Lipids may provide an energy content between about 25% and about 40% of the supplement.

The supplement may comprise any number of optional additional ingredients, including conventional food additives, for example acidulants, thickeners, buffers or agents for pH adjustment, chelating agents, colorants, emulsifiers, excipients, flavor agents, minerals, osmotic agents, a pharmaceutically acceptable carrier, preservatives, stabilizers, sugars, sweeteners, texturizers and/or vitamins. The optional ingredients can be added in any suitable amount.

The supplement can be in any oral nutritional form, e.g. as a health drink, as a ready-made drink, optionally as a soft drink, including juices, milk-shake, yogurt drink, smoothie or soy-based drink, in a bar, or dispersed in foods of any sort, such as baked products, cereal bars, dairy bars, snack-foods, soups, breakfast cereals, muesli, candies, tabs, cookies, biscuits, crackers (such as rice crackers), and dairy products.

The supplement may be in the form of tablets, capsules, pastilles or a liquid, for example. The supplement may further contain protective hydrocolloids (such as gums, proteins, modified starches), binders, film forming agents, encapsulating agents/materials, wall/shell materials, matrix compounds, coatings, emulsifiers, surface active agents, solubilizing agents (oils, fats, waxes, lecithins or the like), adsorbents, carriers, fillers, co-compounds, dispersing agents, wetting agents, processing aids (solvents), flowing agents, taste masking agents, weighting agents, jellifying agents and gel forming agents.

EXAMPLES

The following experimental examples present scientific data developing and supporting the concept of peri-operative consumption of specialized immunonutrition drinks to prevent cachexia, regulate the adaptive immune response via blunting the expansion of myeloid-derived suppressor cells, and/or resolve inflammation after surgery.

Example 1

57 patients were screened, 25 patients enrolled in the study, and 17 completed the study. Men with bladder cancer scheduled for RC were randomized to receive an immunonutrition drink containing arginine, fish oil, and nucleotides (IMD) (n=9) or an iso-caloric placebo (ONS) (n=7) for 5 days before and after surgery. The IMD provided 1,020 kcals, 14.1 g arginine, 3.3 g eicosapentaenoic acid (EPA) and docosahexaenoic acid (DHA), and 1.2 g dietary nucleotides per day. The ONS provided 1,080 kcals, 1.8 g arginine, 0.0 g EPA and DHA, and 0.0 g dietary nucleotides per day.

Blood was assayed at baseline, surgery, 2 days after surgery, 15 days after surgery, and 30 days after surgery (FIG. 1). The baseline characteristics of each group are shown in the table in FIG. 2.

The percentage of peripheral blood mononuclear cells that are MDSC (Lin-CD11b+CD33+) was determined by flow cytometry. Plasma arginine was measured by Ultraperformance® Liquid Chromatography. Differences in MDSC counts and plasma arginine between the two groups were assessed using the repeated measures linear mixed model framework. MDSC count increased more prominently in the control ONS group (+101±113) than in the IMD group (+19±25) ($P<0.02$). (FIG. 3). Arginine concentrations showed a nonsignificant trend of decreasing more in the control ONS group (−16±9 μmol/L) than the IMD group (−11±37 μmol/L) 2 days after surgery (FIG. 4).

Post-operative complications were recorded for thirty days after surgery ("early complications"). Fisher's Exact test was used to compare minor complications. Fewer patients in the IMD group (n=1, 11%) experienced complications compared to the control ONS group (n=4, 57.1%), trending toward statistical significance (P=0.10). Ileus was the complication recorded for the IMD group, while wound infections (n=2), ileus (n=1), and pneumonia (n=1) were recorded in the control ONS group. The early surgical complications are set forth in the table in FIG. 5, as well as complications at ninety days after surgery ("late complications").

The control ONS group lost more weight than the IMD group (P=0.02). The mean difference in weight from pre-operative visit to post-operative day (POD) 14 was −9.4 kg in the control ONS group and −4.8 kg in the IMD group. The mean difference in weight from preoperative visit to POD 30 was −6.2 kg in the control ONS group and −2.8 kg in the IMD group.

To further explore the effects of IMD in muscle invasive bladder cancer patients undergoing radical cystectomy (RC), pathways that define helper T cell differentiation and surgery-induced cachexia were examined. Men received IMD (n=3) or placebo drinks (n=3) to consume five days before and five after surgery. Two days after RC surgery, CD4+ T cells were purified from blood, stimulated with anti-CD3 and anti-CD28, and analyzed by Illumina Next Gen RNA Sequencing. Differences in mRNA levels were assessed using the Exact Test based on the negative binomial distribution. Multiple testing adjustments were applied using the Benzamini and Hochberg method.

Figure 6:
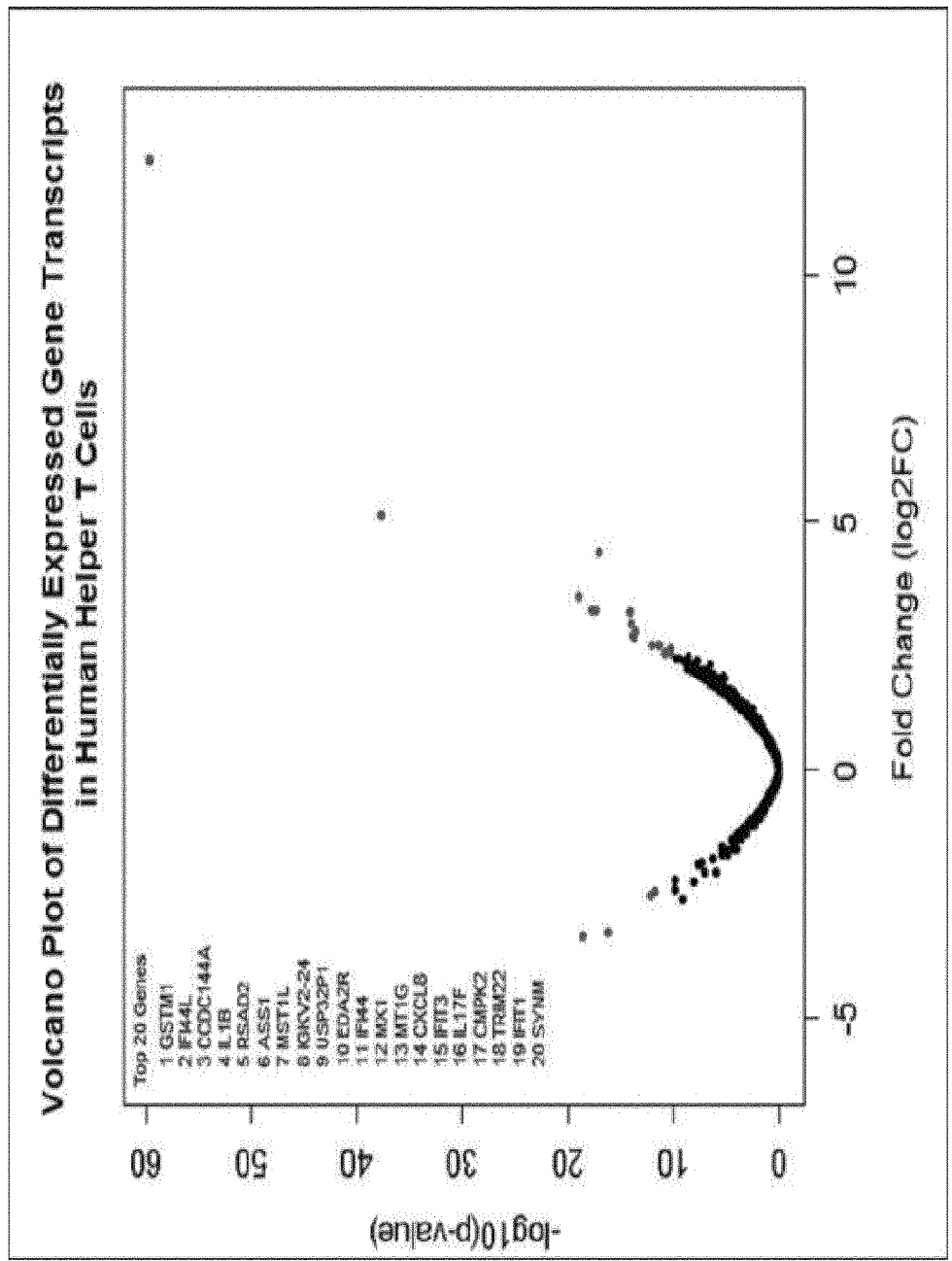
FIG. 6 is a graph showing mRNA expression in the inventive group relative to the control group in the first experimental study disclosed herein.

Compared to the control ONS group, 46 mRNA transcripts were down-regulated and 175 mRNA transcripts were up-regulated in the IMD group (FIG. 6). The mRNA encoding for inflammatory cytokines IL-1β, IL-6, IL-17, and IL-31 were decreased in cells in the IMD group, as compared to control the ONS group (FDR<0.05). Furthermore, mRNA levels for IL-4 and IL-5 trended downward in the IMD group (FDR<0.11). Pathway analysis indicated cells from the IMD group had lower NF-κB activity than placebo. IMD intake before and after RC surgery led to a reduction in mRNA levels of cytokines associated with helper T cell activity, particularly the pro-inflammatory cytokines. Thus, IMD may reduce the inflammatory environment after surgery, and reduce post-operative complications, especially cachexia.

Together these results demonstrate the feasibility of post-operative feeding by mouth; IMD appears to attenuate MDSCs and stabilize plasma arginine; fewer post-operative complications occur in the IMD group; the IMD group shows less profound weight loss; and significant molecular effects on inflammation and immune function are observed.

Figure 7:
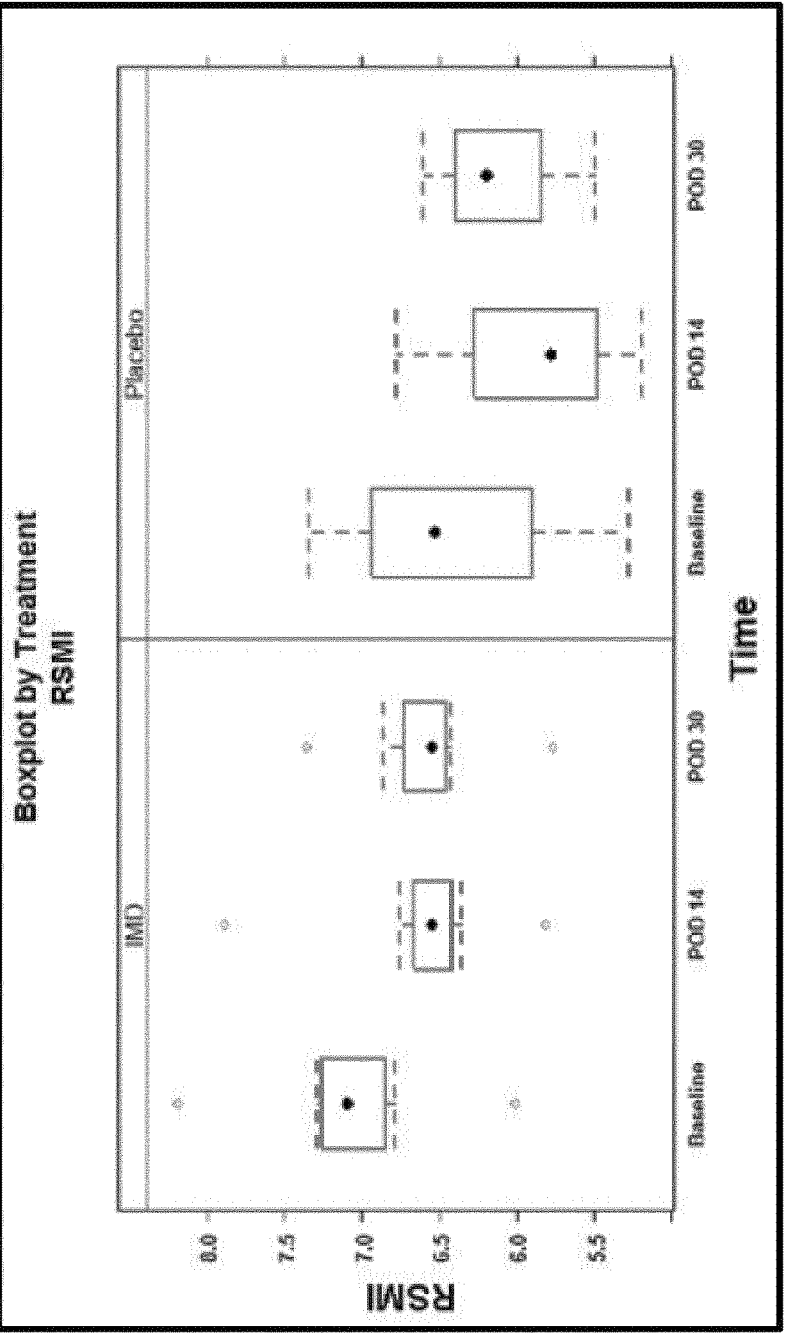
FIG. 7 is a graph showing the relative skeletal muscle index (RSMI) in the inventive group and the control group over time in the first experimental study disclosed herein.

Additionally, changes in non-bone lean tissue (muscle mass) were assessed by dual-energy X-ray Absorptiometry (DXA) (GE Lunar iDXA, Software version 13.5, Madison, WI) at baseline, 30 days, 90 days and 6 months (FIG. 7). The data shows a signal toward preserving the relative skeletal muscle index (RSMI) in the IMD group compared to the control ONS group.

Figure 8:
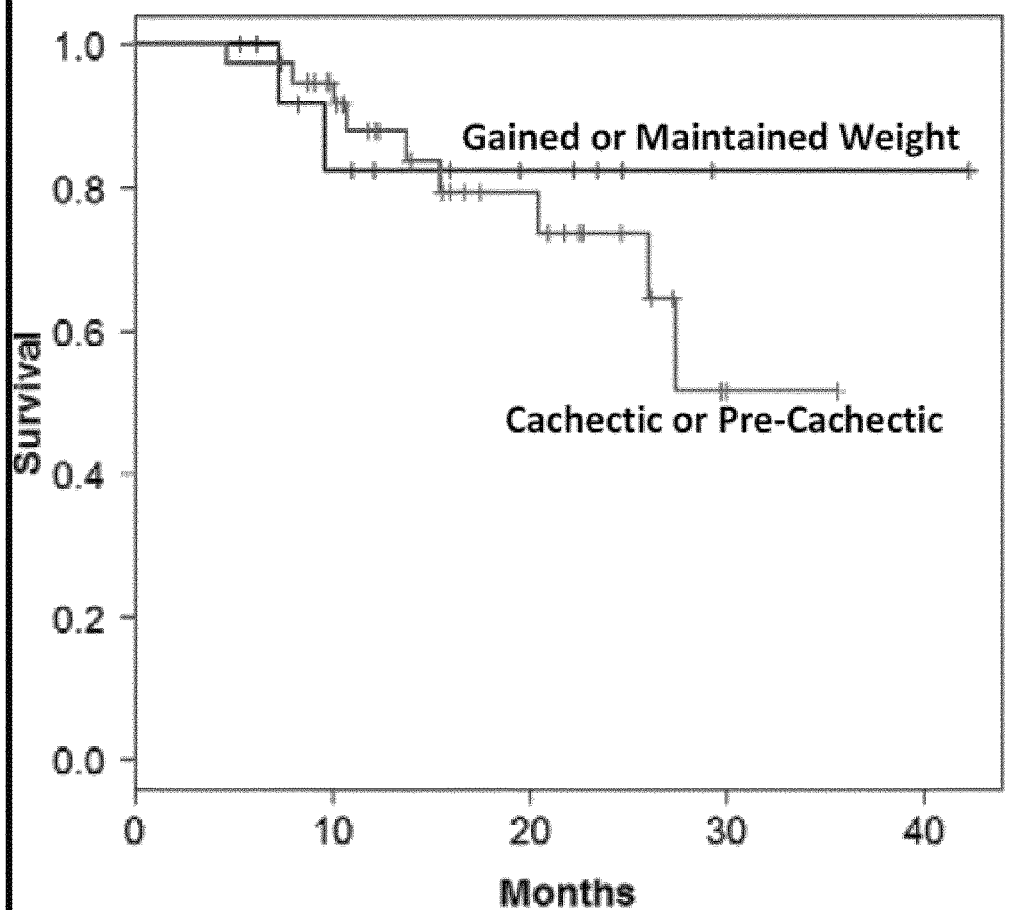
FIG. 8 is a graph of retrospective data showing post-surgery survival rates over time in individuals who gained or maintained rate and in individuals who were cachectic or pre-cachectic.

Preventing the loss of lean body mass improves survival and outcomes. Specifically, retrospective data prior to this study suggests that patients who lose weight after surgery are less likely to survive (FIG. 8). This retrospective data shows that patients lose an average of 5% of their body-weight after radical cystectomy and appear to lose skeletal muscle. Given that loss of muscle is correlated with increases in IL-6 and inflammation markers, it is likely that the catabolic response to surgery is driven by the host systemic inflammatory response. A more balanced immune state and downregulated acute-phase protein response is hypothesized to lead to less skeletal muscle wasting and better health outcomes.

Example 2

To further compare the effects of IMD to the control ONS, a second study was conducted. Twenty-nine men scheduled to undergo RC for primary bladder cancer were randomized using a sequence generated by the statistician to either IMD or the ONS control group. Blocked randomization using blocks of 10 were used to allocate participants according to a computer-generated randomization list with a predetermined ratio of 1:1. The statistician was not involved in the study implementation. The allocation list was only accessible to the study coordinator via a password-protected file.

The cartons were wrapped with opaque tape and coded numerically. Health care providers and data collectors were blinded to the intervention. The study was restricted to men to reduce the variability in RC outcomes known to exist between genders. Exclusion criteria were swallowing difficulties, metastasis, >10% weight loss in past six months, body mass index <18.5, viral infection, immune deficiency, gout, or relevant food allergies. Patients were instructed to consume three cartons per day for five days before and five days after RC. Anesthetic, surgical, and post-operative management were provided according to the standard pathways of the academic institution and consistent with Enhanced Recovery After Surgery pathways. The primary end point of the study was the immune response to surgery (change in total MDSC counts); secondary end points were post-operative complication and infection rates.

Blood was collected at baseline, during surgery (3 hours after first incision), and on post-operative days 2, 14, and 30. The ratio of the absolute neutrophil-to-lymphocyte count was abstracted from the complete blood count with differential. MDSC (Lin-CD11b+CD33+) counts were determined by flow cytometry and sorted into phenotypes using published methods. Differences in the immune response were assessed longitudinally using the generalized linear model, SAS procedure GLIMMIX with spatial power covariance structure (SP[POW]).

Post-operative complications were defined as early ($\leq 30$ days) versus late (31-90 days). Complications were graded according to the Clavien-Dindo scheme; a post-operative ileus was defined as a delay in institution of a regular diet$\geq 5$ days post-operatively. Infectious complications were defined by the need for intervention or prescription of non-prophylactic antibiotics. Complication and infection rates between groups were compared by a chi-square test using the intention-to-treat principle. Logistic regression was used to evaluate the association between MDSC expansion and infection rates. A $p<0.05$ was considered statistically significant.

All adverse events related to the study intervention were gastrointestinal. Participants receiving IMD were more likely to self-report post-operative diarrhea (p=0.008). No one stopped treatment because of adverse events, and none of the reported adverse events were graded as serious. MDSC counts were significantly different between the IMD and ONS groups over time (p=0.005) (FIG. 9A). Monocytic MDSC (M-MDSC) phenotype counts were significantly different between the IMD and ONS groups over time (p=0.008) (FIG. 9B). Granulocytic and immature phenotypes did not differ significantly between groups. Neutrophil:lymphocyte ratio (NLR) was significantly lower in the IMD group compared with the ONS group three hours after incision (p=0.039), but NLR did not differ significantly between the IMD and ONS groups over time.

FIG. 10 shows post-operative complication and infection rates. No differences were detected in the early period. Participants receiving IMD had a 33% reduction in post-operative complication rate (95% confidence interval [CI], 1-64; p=0.060) and a 39% reduction in infection rate (95% CI, 8-70; p=0.027) during late-phase recovery.

MDSC expansion restrains the activation of T cells and lowers resistance to infection. With every unit increase in MDSC count from surgery to two days post-operatively, the odds of infection rate 90 days after surgery increased by 2.5% (p=0.061).

This study shows that immune response to surgery and late infection rates differ between RC patients receiving IMD versus ONS in the peri-operative period. The M-MDSC subtype appears to be the most responsive phenotype to RC and may be restrained by IMD intake. M-MDSC counts in cancer patients positively correlate with regulatory T-cell counts, and in vitro, M-MDSC mediates T-cell suppression. Fewer post-operative complications and infections in RC patients receiving IMD were reported in this study.

Given that NLR has been suggested as a biomarker for predicting clinical course in surgical populations, the lower NLR response three hours after first incision in the IMD group compared with the ONS group suggests IMD consumption may modulate the acute immune response to surgical stress. The differences in the short-term immune response between IMD and ONS may alter the trajectory of a patient's resistance to infection as time progresses.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method of treating or preventing cachexia induced by at least one of surgery, cancer or infection in a patient who is an individual with bladder cancer scheduled to undergo a radical cystoprostatectomy, the method comprising administering to the patient a specialized immunonutrition supplement comprising a combination of L-arginine, omega-3 fatty acids, vitamin A, and nucleotides, and the specialized immunonutrition supplement is administered to the patient in a daily dose that provides an amount of the omega-3 fatty acids that comprises about 0.5 g to about 10.0 g of eicosapentaenoic acid and docosahexaenoic acid in total per day and that provides at least about 500 µg RE of the vitamin A per day; and the specialized immunonutrition supplement is administered to the patient at least once per day for a time period extending from a pre-operative day that is three to seven days prior to the radical cystoprostatectomy to a post-operative day that is three to seven days after the radical cystoprostatectomy.

2. The method of claim 1, wherein the cachexia is induced by infection.

3. The method of claim 1, wherein the specialized immunonutrition supplement is administered to the patient in a daily dose that provides between about 5 g and about 30 g of the L-arginine per day.

4. The method of claim 1, wherein the specialized immunonutrition supplement is administered to the patient in a daily dose that provides an amount of the omega-3 fatty acids that comprises about 1.0 g to about 5.0 g of eicosapentaenoic acid and docosahexaenoic acid in total per day.

5. The method of claim 1, wherein the specialized immunonutrition supplement is administered to the patient in a daily dose that provides between about 0.5 mg and about 10.0 mg of the nucleotides per day.

6. The method of claim 1, wherein at least a portion of the nucleotides are provided by polymeric yeast RNA and/or derived from yeast RNA.

7. The method of claim 1, wherein the specialized immunonutrition supplement is orally administered to the patient.

8. The method of claim 1, wherein the specialized immunonutrition supplement further comprises an additional component selected from the group consisting of a protein, a carbohydrate, a lipid, and mixtures thereof.

9. The method of claim 1, wherein the bladder cancer is associated with a tumor.

* * * * *